(12) United States Patent
Brain

(10) Patent No.: US 6,918,388 B2
(45) Date of Patent: *Jul. 19, 2005

(54) INTUBATING LARYNGEAL MASK

(75) Inventor: Archibald Ian Jeremy Brain, Surrey (GB)

(73) Assignee: The Laryngeal Mask Company Limited, Victoria (SC)

( * ) Notice: Subject to any disclaimer, the term of this patent is extended or adjusted under 35 U.S.C. 154(b) by 0 days.

This patent is subject to a terminal disclaimer.

(21) Appl. No.: 10/672,768

(22) Filed: Sep. 26, 2003

(65) Prior Publication Data

US 2004/0060564 A1 Apr. 1, 2004

Related U.S. Application Data

(63) Continuation of application No. 09/559,366, filed on Apr. 24, 2000, now abandoned, which is a continuation of application No. 08/901,055, filed on Jul. 25, 1997, now Pat. No. 6,079,409.

(51) Int. Cl.$^7$ ............................................. A61M 16/00
(52) U.S. Cl. ............................. 128/200.26; 128/207.15
(58) Field of Search ....................... 128/200.26, 207.14, 128/207.15; 604/96.01

(56) References Cited

U.S. PATENT DOCUMENTS

| | | | |
|---|---|---|---|
| 2,862,498 A | 12/1958 | Weekes | |
| 3,554,673 A | 1/1971 | Schwartz et al. | |
| 4,231,365 A | 11/1980 | Scarberry | |
| 4,509,514 A | 4/1985 | Brain | |
| 4,553,540 A | 11/1985 | Straith | |
| 4,872,483 A | 10/1989 | Shah | |
| 4,953,547 A | 9/1990 | Poole, Jr. | |
| 4,995,388 A | 2/1991 | Brain | |
| 5,038,766 A | * | 8/1991 | Parker .................... 128/200.26 |

(Continued)

FOREIGN PATENT DOCUMENTS

| | | |
|---|---|---|
| CA | 2067782 | 6/1999 |
| CA | 2012750 | 8/1999 |

(Continued)

OTHER PUBLICATIONS

Brain, "The Laryngeal Mask Airway—A Possible New Solution to Airway Problems in the Emergency Situation," *Archives of Emergency Medicine*, 1984, vol. 1, pp. 229–232.
Brain, "The laryngeal mask airway," *Anaesthesia*, 1985, vol. 40, pp. 356–361.

(Continued)

*Primary Examiner*—Aaron J. Lewis
(74) *Attorney, Agent, or Firm*—Wilmer Cutler Pickering Hale and Dorr LLP

(57) ABSTRACT

An intubating LMA construction features a rigid airway tube wherein curvature in a single plane establishes essentially an arcuate path of angular extent in the preferred range of 130°, plus or minus 5°, which I have found to be in substantial anatomical conformance with the adult human's airway path, between a proximal end of the arc at substantial register with the longitudinal midpoint of the hard palate, and a distal end that faces and is at short offset from the glottic aperture, it being understood that my findings apply to suitably quantified allowance for variations in patient-head anatomy, as is for example customary for different sizes of LMA devices, each of which is adapted to serve one of five selected patient-size ranges. The proximal end of the rigid tube is suitably a short straight portion which is tangentially and integrally related to the proximal end of the arc. And the distal end of the arc is fitted with flexible mask structure of preferably elastomeric material such as silicone rubber, wherein an internal ramp formation within the mask structure assures a limited but important measure of further and stabilized guidance of an ET which has emerged from the distal end of the rigid tube, such that unguided displacement of the ET (i.e., beyond the ramp) is oriented to target safe entry of the ET into the glottic opening.

47 Claims, 3 Drawing Sheets

U.S. PATENT DOCUMENTS

| | | | | |
|---|---|---|---|---|
| 5,241,956 A | * | 9/1993 | Brain | 128/207.15 |
| 5,249,571 A | | 10/1993 | Brain | |
| 5,282,464 A | | 2/1994 | Brain | |
| 5,297,547 A | | 3/1994 | Brain | |
| 5,303,697 A | * | 4/1994 | Brain | 128/200.26 |
| 5,305,743 A | * | 4/1994 | Brain | 128/207.15 |
| 5,339,805 A | | 8/1994 | Parker | |
| 5,339,808 A | | 8/1994 | Don Michael | |
| 5,355,879 A | | 10/1994 | Brain | |
| 5,391,248 A | | 2/1995 | Brain | |
| 5,529,582 A | | 6/1996 | Fukuhara | |
| 5,569,219 A | | 10/1996 | Hakki et al. | |
| 5,584,290 A | | 12/1996 | Brain | |
| 5,599,301 A | | 2/1997 | Jacobs et al. | |
| 5,623,921 A | | 4/1997 | Kinsinger et al. | |
| 5,632,271 A | | 5/1997 | Brain | |
| RE35,531 E | | 6/1997 | Callaghan et al. | |
| 5,653,229 A | | 8/1997 | Greenberg | |
| 5,655,528 A | | 8/1997 | Pagan | |
| 5,682,880 A | | 11/1997 | Brain | |
| 5,711,293 A | | 1/1998 | Brain | |
| 5,743,254 A | | 4/1998 | Parker | |
| 5,746,202 A | | 5/1998 | Pagan | |
| 5,771,889 A | | 6/1998 | Pagan | |
| 5,791,341 A | * | 8/1998 | Bullard | 128/207.15 |
| 5,850,832 A | * | 12/1998 | Chu | 128/200.26 |
| 5,865,176 A | | 2/1999 | O'Neil | |
| 5,878,745 A | | 3/1999 | Brain | |
| 5,881,726 A | | 3/1999 | Neame | |
| 5,896,858 A | | 4/1999 | Brain | |
| 5,915,383 A | | 6/1999 | Pagan | |
| 5,937,860 A | * | 8/1999 | Cook | 128/207.15 |
| 5,979,445 A | | 11/1999 | Neame et al. | |
| 5,983,897 A | | 11/1999 | Pagan | |
| 5,988,167 A | | 11/1999 | Kamen | |
| 6,003,510 A | | 12/1999 | Anunta | |
| 6,003,514 A | * | 12/1999 | Pagan | 128/207.15 |
| 6,012,452 A | | 1/2000 | Pagan | |
| 6,021,779 A | | 2/2000 | Pagan | |
| 6,050,264 A | | 4/2000 | Greenfield | |
| 6,055,984 A | | 5/2000 | Brain | |
| 6,070,581 A | * | 6/2000 | Augustine et al. | 128/207.15 |
| 6,079,409 A | * | 6/2000 | Brain | 128/200.26 |
| D429,811 S | | 8/2000 | Bermudez | |
| 6,095,144 A | * | 8/2000 | Pagan | 128/207.15 |
| 6,116,243 A | | 9/2000 | Pagan | |
| 6,119,695 A | * | 9/2000 | Augustine et al. | 128/207.15 |
| 6,240,922 B1 | * | 6/2001 | Pagan | 128/207.15 |
| 6,386,199 B1 | * | 5/2002 | Alfery | 128/207.15 |
| 6,390,093 B1 | | 5/2002 | Mongeon | |
| 6,427,686 B2 | * | 8/2002 | Augustine et al. | 128/200.26 |
| 6,439,232 B1 | * | 8/2002 | Brain | 128/207.15 |
| 6,631,720 B1 | | 10/2003 | Brain | |
| 6,668,821 B2 | * | 12/2003 | Christopher | 128/200.26 |
| 6,698,428 B2 | | 3/2004 | Brain | |
| 6,698,430 B2 | * | 3/2004 | Van Landuyt | 128/207.15 |
| 6,705,318 B1 | | 3/2004 | Brain | |
| 6,722,368 B1 | * | 4/2004 | Shaikh | 128/207.15 |
| 6,729,325 B2 | * | 5/2004 | Alfery | 128/200.26 |
| 6,792,948 B2 | | 9/2004 | Brain | |
| 2003/0037790 A1 | | 2/2003 | Brain | |
| 2003/0051734 A1 | | 3/2003 | Brain | |
| 2003/0101998 A1 | | 6/2003 | Zocca et al. | |
| 2003/0136413 A1 | | 7/2003 | Brain et al. | |
| 2003/0172925 A1 | | 9/2003 | Zocca et al. | |

FOREIGN PATENT DOCUMENTS

| | | |
|---|---|---|
| EP | 0 389 272 | 9/1990 |
| EP | 0 402 872 | 12/1990 |
| EP | 0 294 200 | 4/1992 |
| EP | 0 580 385 | 5/1996 |
| EP | 0 712 638 | 5/1996 |
| EP | 0 732 116 | 9/1996 |
| EP | 0 796 631 | 9/1997 |
| EP | 0 845 276 | 6/1998 |
| EP | 0 865 798 | 9/1998 |
| EP | 0 922 465 | 6/1999 |
| EP | 1 125 595 | 8/2001 |
| GB | 2111394 | 12/1982 |
| GB | 2205499 | 6/1987 |
| GB | 2317342 | 8/1997 |
| GB | 2317830 | 9/1997 |
| GB | 2318735 | 10/1997 |
| GB | 2319478 | 10/1997 |
| GB | 2321854 | 1/1998 |
| GB | 2323289 | 2/1998 |
| GB | 2323290 | 3/1998 |
| GB | 2323291 | 3/1998 |
| GB | 2323292 | 3/1998 |
| GB | 2359996 | 9/2001 |
| JP | 10118182 | 5/1998 |
| JP | 10216233 | 8/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO 91/03207 | 3/1991 |
| WO | WO 91/07201 | 5/1991 |
| WO | WO 91/12845 | 9/1991 |
| WO | WO 92/13587 | 8/1992 |
| WO | WO 95/33506 | 12/1995 |
| WO | WO 97/12640 | 4/1997 |
| WO | WO 97/12641 | 4/1997 |
| WO | WO 98/16273 | 4/1998 |
| WO | WO 99/06093 | 2/1999 |
| WO | WO 00/22985 | 4/2000 |
| WO | WO 00/23135 | 4/2000 |
| WO | WO 00/61212 | 10/2000 |

OTHER PUBLICATIONS

Brain, "Three cases of difficult intubation overcome by the laryngeal mask airway," *Anaesthesia*, 1985, vol. 40, pp. 353–355.

DeMello, et al., "The use of the laryngeal mask airway in primary anaesthesia," *Anaesth. Corresp.* (1990) 45,9:793.

Hickey, et al., "Cardiovascular response to insert of Brain's laryngeal mask," *Anesth. Corresp.* 1990, vol. 45, pp. 977–979.

Davies et al., "Laryngeal Mask Airway and Tracheal Tube Insertion by Unskilled Personnel," *The Lancet*, (1990) pp. 977–979.

Brain, "The Laryngeal Mask—A New Concept in Airway Management," *Br. J. Anesth.* (1983), vol. 55, pp. 801–805.

Broderick, "The laryngeal mask airway," (1989) *Anaesthesia*, vol. 44, pp. 238–241.

Inomata, et al., "Transient Bilateral Vocal Cord Paralysis after Insertion of a Laryngeal Mask Airway," *Anesthesiology*, 82:787–788, 1995.

Majumder, et al., "Bilateral Lingual Nerve Injury Following the Use of the Laryngeal Mask Airway," *Anaesthesia*, 1998, vol. 53, pp. 184–186.

Wynn, et al., "Tongue Cyanosis after Laryngeal Mask Airway Insertion," *Anesthesiology*, V. 80, No. 6, Jun. 1994, p. 1403.

Nagai, "Unilateral hypoglossal nerve paralysis following the use of the laryngeal mask airway," *Anaesthesia*, 1994, vol. 49, pp. 603–604.

Brain, et al., "A new laryngeal mask prototype," *Anaesthesia*, 1995, vol. 50, pp. 42–48.

Burgard, et al., 'The Effect of Laryngeal Mask Cuff Pressure on Postoperative Sore Throat Incidence,' *J. of Clinical Anesthesia* 8:198–201, 1996.

Benumol, "Laryngeal Mask Airway and the ASA Difficult Airway Algorithm," *Anesthesiology* 1996:v84 No. 3:686–99.

Pennant, "Comparison of the Endotracheal Tube and Laryngeal Mask in Airway Management by Paramedical Personnel," *Anesth Analg* 1992:74:531–4.

Brimacombe, "The split laryngeal mask airway," p. 639.

Worthington, et al., "Proceedings of the Anaesthetic Research Society," *Br. J. of Anaesthesia* 1995 75:228P–229P.

Heath, "Endotracheal intubation through the Laryngeal Mask—helpful when laryngoscopy is difficult or dangerous," *European Journal of Anaesthesiology* 1991, Suppl. 4, 41–45.

Kambic, et al., "Intubation Lesions of the Larynx," *Br. J. Anasth*. 1978, 50, 587–590.

Abdelatti, "A cuff pressure controller for tracheal tubes and laryngeal mask airway," *Anaesthesia*, 1999, 54 pp. 981–986.

Muthuswamy, et al., "The Use of Fuzzy Integrals and Bispectral Analysis of the Electroencephalogram to Predict Movement Under Anesthesia," *IEEE Transactions on Biomedical Engineering*, vol. 46, No. 3, Mar. 1999, pp290–299.

Glen, "The development of 'Diprifusor': a TCI system for propofol," *Anaesthesia* 1998, 53, Suppl. 1, pp. 13–21.

Gray et al., " Development of the technology for 'Diprifusor' TCI systems," *Anaesthesia* 1998, 53, Suppl. 1, pp. 22–27.

Engbers, "Practical use of 'Diprifusor' systems", *Anaesthesia* 1998, 53, Suppl. 1, pp. 28–34.

Doyle et al., "Intraoperative Awareness: A Continuing Clinical Problem," http://doyle.ibme.utoronto.ca/anesthesia/aware.htm.

Eriksson, et al., "Functional Assessment of the Pharynx at Rest and during Swallowing in Partially Paralyzed Humans," *Anesthesiology* vol. 87, No. 5, Nov. 1997, pp. 1035–1042.

Cuff–Pressure–Control CDR 2000, LogoMed.

Seegobin, et al., "Endotrachael cuff pressure and tracheal mucosal blood flow: endoscopic study of effects of four large volume cuffs," *British Medical Journal*, vol. 288, Mar. 31, 1984.

Raeder, et al., "Tracheal tube cuff pressures," *Anaesthesia*, 1985, vol. 40, pp. 444–447.

Jacobson et al., A Study of Intracuff Pressure Measurements, Trends and Behaviours in Patients During Prolonged Periods of Tracheal Intubation, *Br. J. Anaesth*. 1981, 53, 97.

Willis, et al., "Tracheal tube cuff pressure," *Anaesthesia*, 1988, vol. 43, pp. 312–314.

Miller, "A pressure regulator for the cuff of a tracheal tube," *Anaesthesia*, 1992, vol. 47, pp. 594–596.

Patel, et al, "Trachael tube cuff pressure," *Anaesthesia*, 1984, vol. 39, pp. 862–864.

Pippin, et al., "Long–term tracheal intubation practice in the United Kingdom", *Anaesthesia*, 1983, vol. 38, pp. 791–795.

Bernhard, et al., "Adjustment of Intracuff Pressure to Prevent Aspiration," *Anesthesiology* v. 50 No. 4:363–366, 1979.

Bernhard, et al., "Physical Characteristics of and Rates of Nitrous Oxide Diffusion into Trachael Tube Cuffs," *Anesthesiology* 48:413–417 1978.

Craven, "Prevention of Hospital–Acquired Pneumonia: Measuring Effect in Ounces, Pounds, and Tons, "*Annals of Internal Medicine*, vol. 122, No. 3, pp. 229–231 Feb. 1, 1995.

Lindholm, "Prolonged Endotracheal Intubation," *ACTA Anaesthesiologica Scandinavica* 1969 vol. 33 32–46.

Caplan R.A., Posner K.L., Wend R.J., Cheney F.W., " Adverse respiratory events in anesthesia: a closed claims analysis", *Anesthesiol*. 1990. 72:828–833.

Benumof J.L., "Management of the difficult airway with special emphasis on awake tracheal intubation," *Anesthesiol*. 1991. 75;6:1087.

Kapila A., Addy E.V., Verghese C., Brain A.J., "Intubating LMA: a preliminary assessment of performance", *British Journal of Anaesthesia*, 1995; 75:228–229 (Abstract).

* cited by examiner

INTUBATING LARYNGEAL MASK

RELATED APPLICATIONS

This application is a continuation of abandoned U.S. patent application Ser. No. 09/559,366, filed 24 Apr. 2000, which is a continuation of U.S. Pat. No. 6,079,409, issued 27 Jun. 2000 (application Ser. No. 08/901,055, filed 25Jul. 1997).

BACKGROUND OF THE INVENTION

The invention pertains to endotracheal-device placement in a patient requiring assured airway access, for breathing or anaesthetic purposes, for example, after the patient has lost consciousness with resulting compromise to the air passages, which can be life-threatening, if the airway access is not quickly and assuredly accomplished.

Endotracheal intubation using a laryngoscope is a relatively skilled procedure and inevitably involves distortion of the anatomy in order to bring the glottis into the line of sight. In addition, an endotracheal tube (ET) is designed for ease of passage when the anatomy is thus distorted; thus, curvature of the ET does not correspond with the contours of the relaxed anatomy of the patient's upper airway. Because it is not always possible or desirable to distort the anatomy, the so-called "difficult" airway remains an important cause of mortality and morbidity in anaesthesia, in spite of a plethora of intubating aids and difficult-airway algorithms.

The laryngeal mask (LMA) has found a place in this arena, but suffers from the disadvantage that its airway tube is too long and narrow to act as an acceptable conduit for intubation, in that it cannot be removed easily from the ET, once intubation has been accomplished. In addition, the mask-aperture bars (MAB) of an LMA may obstruct or deflect ET passage. Nevertheless, the LMA has the advantage that ventilation can usually be maintained, whether or not the patient can be intubated. Examples of LMA devices in prior-art patents are to be found in U.S. Pat. Nos. 4,509,514; 4,995,388; 5,241,956; 5,303,697*, 5,355,879; 5,477,851* (now Reissue patent Re. No. 35,531*); and also in pending U.S. application Ser. No. 08/826,563, filed Apr. 4, 1997*. Of these patent disclosures, those just identified by asterisk (*) deal in one way or another with various structural improvements to facilitate use of an LMA as an aid to intubation.

A "neutral" head position is achieved when the head and neck are positioned, as by a pillow, so as to correspond with the patient's head/neck relation when the patient is standing upright.

U.S. Pat. No. 5,303,697 discloses use of an intubating LMA featuring a rigid stainless-steel airway tube with an inflatable mask at its distal end. The point of the invention was to adopt as thin as possible tube-wall thickness, for purposes of accommodating a range of ET diameters, and to enable manipulation of the placement of the distal mask. The two embodiments of this patent show curvature of the rigid tube to be of differing arcuate extent, namely, either (i) a right angle or (ii) somewhat less than a right angle; and my experience in working with either of these configurations is that distortion of the anatomy was needed, e.g., by the anesthesiologist lifting the patient's neck and extending the head to seek an accommodating non-neutral* variation of spine curvature in the neck region, in order to achieve suitable conditions for LMA placement and intubation through the LMA. Such manoeuvering has at least the disadvantages of (a) requiring full mobility of the bones of the neck, and (b) inviting neurological damage if the patient has sustained a neck injury.

BRIEF STATEMENT OF THE INVENTION

It is an object of the invention to provide an improved LMA construction, with specific applicability to intubation of a patient with an ET or other device.

Specific objects are to achieve the above object with an improved construction that features a rigid airway tube which accommodates natural anatomical curvature and:

(i) in which the need for head and neck manipulation can be avoided, during mask insertion and placement and during intubation;

(ii) in which the need for distortion of the anterior pharyngeal anatomy by a laryngoscope can be avoided;

(iii) in which the intubating laryngeal mask, as a unit, can be self-retaining at an anatomically correct installed position, with minimum local stress on any part of adjacently contacted anatomy;

(iv) in which the larynx can be "masked" by the LMA device without requiring finger-insertion into a patient's mouth;

(v) in which the intubation guide is easily removable without head/neck manipulation or distortion of anterior or posterior anatomical structure;

(vi) in which a more anatomically appropriate ET can be accommodated; and (vii) in which an intermediate airway is available, prior to or during intubation attempts, or following extubation under deep anaesthesia.

The invention achieves the foregoing objectives and other advances in an intubating LMA construction which features a rigid airway tube wherein curvature in a single plane establishes essentially an arcuate path of angular extent in the range of 100° to 145°, a preference being indicated for the range 125° to 135° which I have found to represent normal anatomy in a neutral position; more specifically, I have found the range 125° to 135° to be in substantial anatomical conformance with the airway path of the adult human. The rigid tube extends between a proximal end of the arc—at substantial register with the longitudinal midpoint of the hard palate, and a distal end that faces and is at short offset from the glottic aperture, it being understood that my findings apply to suitably quantified allowance for variations in patient-head anatomy, as is for example customary for different sizes of LMA devices. The proximal end of the rigid tube is suitably a short straight portion which is tangentially and integrally related to the proximal end of the arc. And the distal end of the arc is fitted with flexible mask structure of preferably elastomeric material such as silicone rubber, wherein an internal ramp formation within the mask structure assures a limited but important measure of further and stabilized guidance of an ET which has emerged from the distal end of the rigid tube, such that unguided displacement of the ET (i.e., beyond the ramp) is oriented to target safe entry of the ET into the glottic opening. Stated in other words, the included angle of ET guidance by the preferred embodiment of the invention is approximately 130°, plus or minus 5°, between (a) the "launch" direction of an ET emerging from ramp guidance and (b) the orientation axis of the straight proximal-end portion of the rigid tube.

BRIEF DESCRIPTION OF THE DRAWINGS

The invention will be described in detail for preferred embodiments, in conjunction with the accompanying drawings, in which.

DETAILED DESCRIPTION

Figures 1, 3:
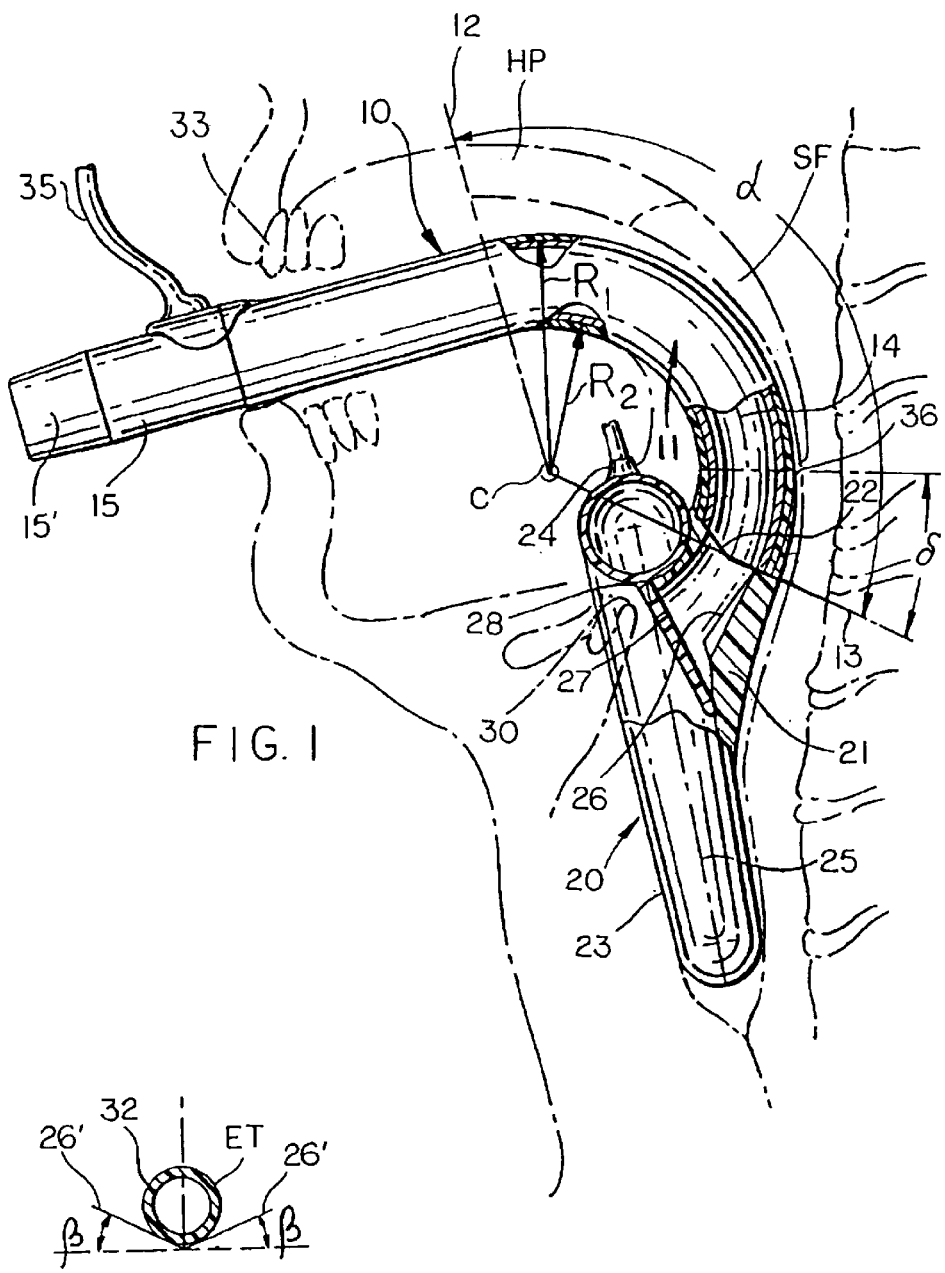
FIG. 1 is a simplified fragmentary view in side elevation and in partial section, taken in the vertical plane of symmetry, showing an intubating laryngeal mask of the invention, in schematically suggestive context of relevant features of a patient's head/neck anatomy.
FIG. 3 is a schematic sectional view taken at the distal end of ramp structure, provided at the distal end of ET guidance by the device of FIGS. 1 and 2, the section being taken in a plane normal to the path of ET guidance, to show ramp stabilization of the ET.

In FIG. 1, an intubating laryngeal-mask (ILM) device 10 of the invention is shown installed in and self-retained by relevant features of a patient's oral anatomy. An anatomically curved rigid tube portion 11 of device 10 is suitably of bent stainless-steel tubing which may be of 13-mm minimum internal diameter, in order to accept insertion of a cuffed 8-mm endotracheal tube (ET). The curved portion 11 is suitably conformed to a circular arc a of preferably 130°±5°, extending from a proximal limit 12 of tube curvature to a distal limit 13 of tube curvature, the curvature being along a central axis 14 of airway passage and in a first (or vertical) geometric plane of symmetry; the maximum or outer radius $R_1$ of tube (11) curvature is suitably 41.5 mm, for use by a large fraction of the adult population, for whom the minimum or inner radius $R_2$ of curvature is about 27 mm.

At the proximal limit 12 of curved portion 11, a straight proximal end portion 15 is an integrally formed part of the same tubing, having tangential connection to the proximal end of the arc at location 12, which is in register with substantially the longitudinal mid-point of the patient's hard palate, labeled HP in the drawing. The outer radius $R_1$ of curved portion 11 is shown to substantially conform to concave curvature of the patient's soft palate (SP), as also labeled in the drawing; and the inner radius $R_2$ of curved portion 11 will be understood to conform to convex curvature of the back of the patient's tongue (not shown).

At the distal end 13 of the curved portion 11 of the rigid tube, the central axis 14 of the airway path determined by the tube is directed toward the laryngeal inlet and is in the above-noted first or vertical plane of symmetry, said distal-end limit being at the upper region of the pharynx and at considerable offset from the intended target of ET entry into the glottic aperture, but laryngeal-mask structure 20 carried by the distal end of the rigid tube is internally configured to extend and laterally stabilize the guidance of an inserted ET, for greater assurance of the targeted entry.

The laryngeal-mask structure 20 is of flexibly yieldable elastomeric material, wherein relative thickness determines the relative stiffness or weakness of compliant deformability. Basically, structure 20 comprises a relatively stiff backing plate formation 21 having an inlet-air counterbore formation (shown, but not marked) of arcuately curved extent δ which accounts for telescopic reception and bonding of mask structure 20 to the distal end of tube 11. As shown, the arcuate extent δ of telescopic fit is 20° to 25°, which is sufficient to assure a circumferentially sealed fit and also to fully provide enclosure of a truncated radially inner-end portion of the rigid tube, the truncation being identified 22 in the drawing.

As with prior laryngeal masks, the backing plate will be understood to terminate in a generally elliptical rim of attachment to a peripherally continuous and softly compliant ring formation which, in the preferred form shown is an inflatable ring 23 having means 24 of control connection for air-inflation/deflation purposes. The elliptical rim and ring 23 will be further understood (a) to have lateral symmetry about the vertical plane of symmetry and (b) to lie generally in a second geometric plane 25 which is normal to the first or vertical plane.

Within the backing plate 21, the airway passage of the rigid tube 11 is seen to be effectively extended by a ramp formation 26 of V-section and of progressively increasing depth, beginning at substantially tangential relation to the adjacent end of the tube bore at the outer radial limit ($R_1$) of rigid tube curvature; by reason of its sectional symmetry about the above-noted first geometric plane of symmetry, ramp formation 26 will be seen to serve the dual purpose of stabilizing an ET in the course of its insertional advance beyond the distal end of tube 11, while at the same time providing a substantially shortened offset distance for otherwise unsupported projection of the distal end of an ET, beyond the distal end of ramp formation 26, for better-controlled targeting of ET entry into the glottic opening. FIG. 3 schematically illustrates stabilizing support for an insertionally advancing ET, wherein the Vee of ramp 26 is seen to provide side walls 26' which symmetrically diverge from the central plane of symmetry, the included angle of Vee spread between the walls of ramp formation 26 being suitably in the range 150° to 165°.

The thus-extended advancing guidance of ET insertion is also seen in the drawing to involve ET encounter with a compliantly and effectively hinged tongue formation 27 which may be an integral formation of backing plate 21, but which has been shown with a different direction of cross-hatching, for better identification of parts in the drawing. Tongue formation 27 will be understood to have lateral symmetry about the first geometric plane of symmetry and to be of lateral extent which is less than the bore diameter of tube 11, thus permitting free airway communication to the glottis and through device 10, once ring 23 has been inflated to develop a seal around the laryngeal inlet. However, the compliant hinging of tongue 27 at 28, on an effective hinge axis in plane 25 and perpendicular to the first geometric plane, enables an advancing ET to drive tongue 27 (clockwise, in the sense of the drawing) for deflecting the patient's epiglottis 30 out of the path of the ET as it advances toward the targeted glottic opening.

It will be seen that in general terms, the fact of ET clearance within the inside diameter of the rigid airway tube necessarily means that at exit from the rigid tube, the ET may be at minor misalignment with resepct to the orientation of the central axis 14 at the distal or exit end of the rigid tube; however, the existence and action of the described ramp 26 are such not only to assure ET-centering between opposed ramp walls 26, but also to effect such a ramped deflection of the ET (at ET exit from the ramp) as to substantially offset, minimalize, or correct for the minor misalignment noted at ET exit from the distal end of rigid tube 10. Thus, at launch from the exit end of the ramp, the ET can be more assuredly projected for targeted entry into the glottic opening.

Description of the device of FIG. 1 is completed by identification of a rigid handle 35, secured to the externally projecting proximal end portion 15 of the rigid airway tube 10; handle 35 (preferably sufficiently malleable to enable a technician to adjust handle orientation to suit his individual preference) serves for manual manipulation of tube 10 and its distal mask structure 20; and it will be understood that the open proximal end of portion 15 is adapted by means of an inwardly tapered contour 15' to fit standard ventilating or anaesthetizing equipment for accessing the patient's lungs, as needed. Further preference is indicated for an elastomeric cladding or coating of tube 10, as suggested by cross-hatching 36 in FIG. 1.

Figure 2:
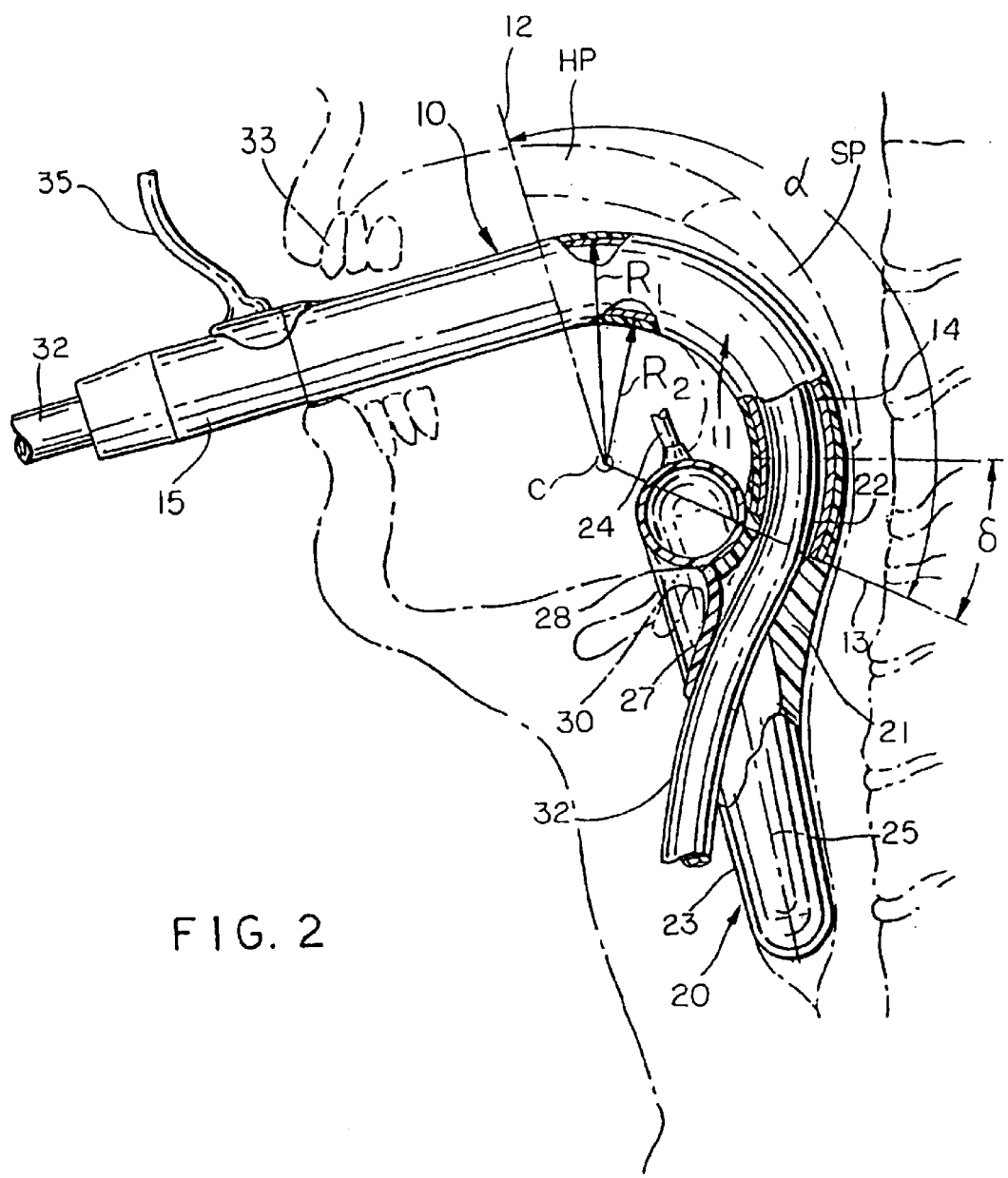
FIG. 2 is a view similar to FIG. 1, to show relevant ET structure that has been guided by the device of FIG. 1.

In use, the device 10 is grasped via handle 35, and the inflatable ring 25 is deflated to define a suitably flexible lip which will smoothly adapt to the patient's airway, as device 10 is being inserted. Once the flexible lip enters the mouth, it naturally and flexibly adapts to hard-palate and soft-palate curvatures on its way to the pharynx, and the truncation 22 of the distal end of the rigid tube enables flexed compression of the mask/tube junction for ease of passage through a narrowed inter-dental gap. In the course of such insertion, it will be appreciated that manipulation of the straight proximal end 15 undergoes a bodily angular displacement (clockwise, in the sense of FIG. 1) about the center C of arcuate portion 11, as said portion 11 is sensed to be in very substantial conformance with the patient's oral anatomy, all the way to the pharynx, thus positioning the distal orientation of tube-11 exit in near-register with the glottic opening. The limit of such angular displacement occurs when the straight proximal end 15 abuts upper tooth structure, e.g., the patient's incisors (33). This event will be recognized as a stop whereby to know that insertion has been completed as far as needed, and ring 23 may be immediately inflated, to establish a peripherally sealed adaptation at and surrounding the laryngeal inlet, with ramp (26) oriented for immediate insertion of an ET device, it being noted that, once ring 23 has been inflated to establish its seal to and around the laryngeal inlet, airway access to the patient's lungs has been provided. On exit from ramp (26) guidance, further displacement of the ET device encounters the compliantly hinged tongue 27, to assure that the epiglottis is lifted out of possible encounter with the advancing ET device, as seen in FIG. 2 for the ET device 32. When the ET device has entered the glottic opening, it can pass the vocal cords and be sealed by inflation of its cuff, as is customary.

After the ET has been sealed in its installed position, the ET can accommodate all patient-ventilating/anaesthetizing purposes. In some clinical circumstances, the intubating laryngeal mask (ILM) can be left in place during the procedure. When the patient has had all use that is needed for the ET, and after its seal cuff has been deflated, ET removal is then a simple matter of extraction via the guide passage established by mask 20. After ET extraction, the device of FIGS. 1 and 2 may then resume its patient-ventilating function, with the hinged tongue 27 compliantly returning to its position of FIG. 1, whereby to avoid epiglottis blocking of the airway; and a resumed intermediate airway can be established for patient ventilation. This procedure may be appropriate when extubation is judged to be best performed while the patient is still under deep anaesthesia. However it is also possible and sometimes desirable to remove the ILM while the ET remains in place. In this case, the ET cuff remains inflated and the ILM cuff is deflated prior to removing the device, following the same circular arc as is followed for insertion. To prevent accidental ET dislodgement, the ET is meanwhile held in place by counterpressure supplied by a short flexible rod abutting against the outer end of the ET as the metal tube is slid over it.

Figure 4:
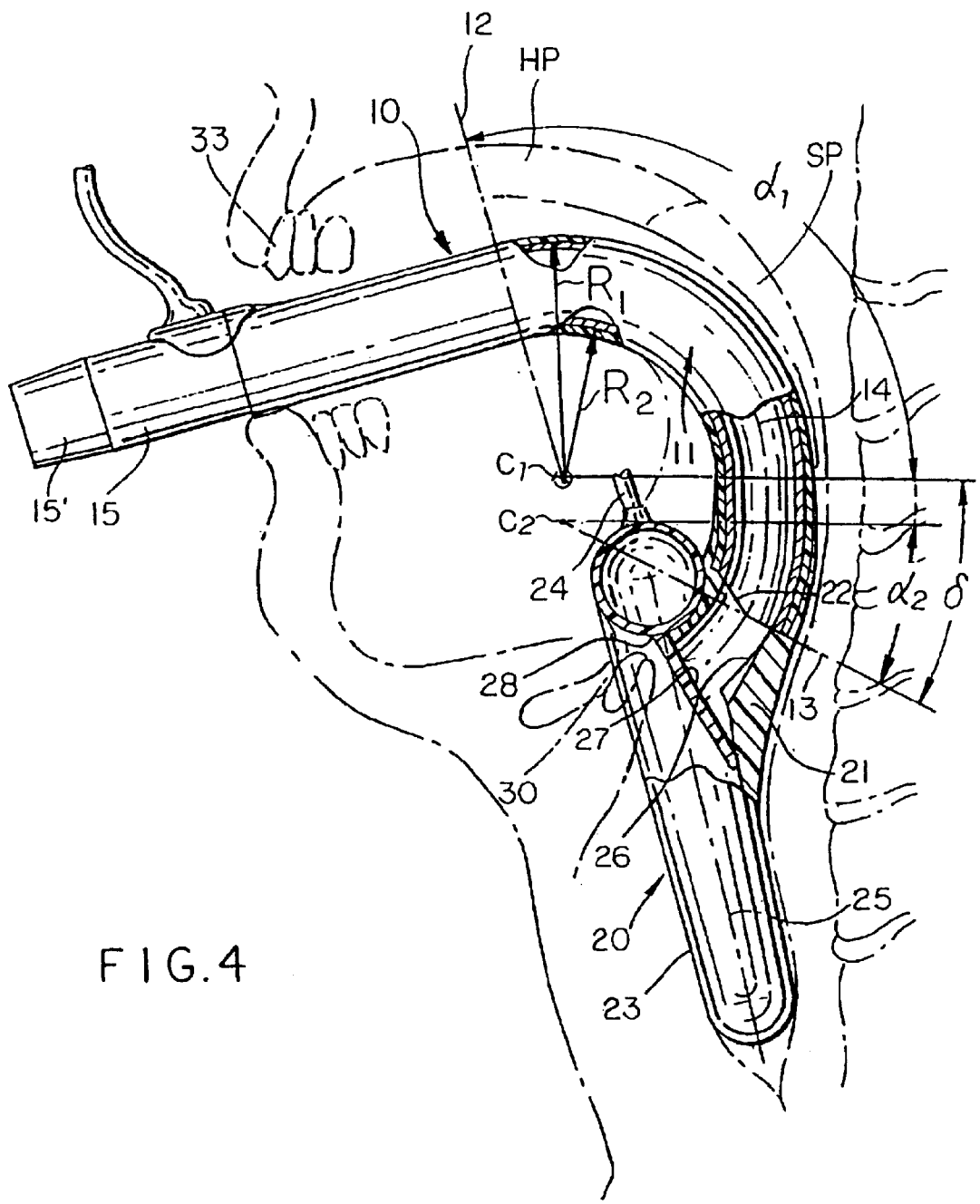
FIG. 4 is a simplified view similar to FIG. 1 to show a modification.

It has been indicated above that, for most cases, a single rigid tube 10 may well serve patients for whom different elastomeric distal-mask components may be fitted, thus serving patients having different oral-cavity geometries and proportions. In some cases, however, and in particular for a patient who can be readily recognized as having an unusually long neck, it is recommended to follow the described rigid-tube configuration of FIGS. 1 to 3, subject to a single modifying departure, at the tube location at which a tangent to the convex outer profile of the tube is locally parallel to (or near-parallel to) the alignment of the patient's vertebrae. Such a condition is illustrated in FIG. 4, wherein the arcuate extent $\alpha$ of rigid tube 10 is seen to have been divided into a first and larger proximal arc $\alpha_1$ about a first center $C_1$, and a second and shorter distal arc $\alpha_2$ about a second center $C_2$. Radius of curvature is the same for both arcs $\alpha_1$ and $\alpha_2$, and the centers $C_1$ and $C_2$ are on a geometric alignment that is essentially parallel to the alignment of locally adjacent vertebrae. Thus, a straight section 37 is effectively aligned essentially parallel to the alignment of adjacent vertebrae, and this straight section 37 is integrally and tangentially united with the adjacent ends of the arcs $\alpha_1$ and $\alpha_2$. In FIG. 4, all other structural features of FIGS. 1 and 2 apply, as described above.

It is noted that the laryngeal opening into and through which the described intubating laryngeal mask provides guided entry is a relatively tolerant anatomical feature for the human adult, in that in terms of a geometric direction suggested by downward extension of line 12 in FIGS. 1 and 2, there is a span between an upper limit established by the epiglottis and a lower limit associated with arytenoid cartilages, wherein said span may extend, typically approximately 20-mm, for target acceptance by the laryngeal opening of an ET launched from the described mask structure. What is accomplished by the structure of FIG. 4 is a predetermined (illustratively 10-mm) further downward offset of the ET-launch point, for the case of a person having a recognized longer-than-usual neck, it being understood that such recognition can be readily deduced from external observation of the patient's "Adam's apple" in relation the patient's maxillary structure.

The described intubating laryngeal-mask devices will be seen to meet all stated objects. Mask removal follows deflation of ring 20, followed by an extraction manoeuver wherein the straight proximal portion undergoes counter-clockwise bodily displacement about the center C. As long as the patient has first been supported in supine position, as with a suitable pillow to assure a "neutral" orientation of the upper region of his spine (i.e., adjacent regions of his head, neck and body), there is no need to manipulate the spine, i.e., the patient's head with respect to his body, either in the course of mask insertion/removal or in the course of ET insertion/removal, thus assuring minimum risk to a patient whose spine has been injured, and thus also removing the major cause of difficulty in intubation of the trachea when immobility of the neck makes it difficult to use a laryngoscope to locate the glottis.

A significant feature of the present invention is the fact that a single manufactured size of the rigid airway tube 10, of bent tubing having a minimum inner diameter of 13-mm, with its arcuate extent in the range 130° plus or minus 5°, and at a minimum outer radius ($R_1$=41.5 mm) about a common center (C), can be assembled with a selected one of three standardized distally fitted LMA inflatable-mask sizes, namely, a selected one of the sizes 3, 4 and 5 which have become standardized on the following basis:

Size 3, for children and small adults, weighing in the range 30 to 50 kg;

Size 4, for adults weighing in the range 50 to 70 kg; and

Size 5, for adults weighing more than 70 kg.

From the point of view of manufacturing economy, this circumstance portends satisfying anatomy requirements of the vast majority of patient's requiring intubation, all using the same size rigid tubing, but fitted with different selected distal inflatable mask sizes, selected from the indicated grouping.

It is also possible that similar economies of rigid airway tube (10) construction can be achieved for remaining standardized LMA sizes, namely, sizes 1, 1.5, 2, and 2.5.

What is claimed is:

1. An incubating laryngeal mask airway device comprising:
   an airway tube having a fixed curve of substantially constant radius in a first geometric plane, the fixed curve is configured to conform to an anatomical curve in a patient between a proximal end at approximately the location of a hard palate and a distal end at approximately a laryngeal inlet, said fixed curve having an arc of an angular extent between 100° and 145°, said airway tube is adapted to be attached to a gas source outside the patient; and,
   a mask structure attached to the distal end of the airway tube, said mask structure includes a backing plate which has a generally elliptical periphery in essentially a second geometric plane which is perpendicular to said first geometric plane and that is adapted to provide an air tight seal around the laryngeal inlet, said attachment between the mask structure and airway cube defines a first acute angle, wherein the airway tube defines a lumen adapted to provide gas from the gas source to the laryngeal inlet.

2. The device of claim 1, in which said angular extent is in the range of 130°±5°.

3. The device of claim 1 in which said mask includes a ramp in the path of advancing intubation beyond the distal end of said tube, said ramp being adapted to substantially maintain an angle of intubation advance toward a glottic opening to facilitate entrance of an endotracheal cube advancing through the opening of the lumen of the device into the patient's glottic aperture.

4. The device of claim 3, in which said ramp is of generally V-section, said ramp having opposing sidewalls that diverge symmetrically with respect to said first geometric plane.

5. The device of claim 4, in which said V-section expands from substantially a single point at exit from the distal end of the curved airway lube, with ramp sidewalls diverging from a central line of symmetry, wherein the central line of symmetry includes said point and is substantially tangent to an outer-radius curvature of the distal end of the bore of said tube.

6. The device of claim 5, wherein the included divergence angle between sidewalls of said ramps is in the range of 150° to 165°.

7. An intubating laryngeal mask airway device comprising:
   an airway tube having a fixed curve of substantially constant radius, the fixed curve is configured to conform to an anatomical curve in a patient between a proximal end at approximately the location of a hard palate and a distal end at approximately a laryngeal inlet, said fixed curve having an arc of an angular extent between 100° and 145°, said airway tube is adapted to be attached to a gas source outside the patient; and,
   a mask structure attached to the distal end of the airway tube, said mask structure includes a backing plate which has a generally elliptical periphery that is adapted to provide an air tight seal around the laryngeal inlet, said attachment between the mask structure and airway tube defines an acute angle, wherein the airway tube defines a lumen adapted to provide gas from the gas source to the laryngeal inlet,
   wherein said mask includes a compliantly hinged tongue that is normally disposed diametrically across the distal end of said path and is adapted to deflect the epiglottis upon advance of intubation beyond said distal end.

8. The device of claim 7, wherein the device is further defined by the distal end of said tube having a telescoping fit to the airway passage of said backing plate, and in which said distal end is truncated at a second acute angle to said second geometric plane, the direction of said second acute angle with respect to said second geometric plane being opposite to the direction of said first acute angle.

9. The device of claim 7, in which the proximal-end portion of said tube has at least a portion that is straight.

10. The device of claim 7 in which said lube has an outer-surface cladding of yieldable elastomeric material.

11. The device of claim 7, in which an inflatable ring continuously surrounding and connected to the periphery of said backing plate is adapted for sealing conformance of said mask structure to the laryngeal inlet.

12. The device of claim 7, in which said fixed curve includes an intermediate locale for which a geometric tangent to said fixed curve is substantially parallel to adjacent patient backbone alignment, and in which an otherwise continuous arcuate development of said fixed curve is divided into proximal and distal regions which are integrally and tangentially formed with a substantially straight intermediate region of predetermined extent that is substantially parallel to said adjacent patient backbone alignment.

13. The device of claim 12, in which said proximal region is arcuate about a first center in said first geometric plane and said distal region is arcuate about a second center in said first geometric plane, said centers being spaced from each other on a geometric alignment which is substantially parallel to said substantially straight intermediate region.

14. The device of claim 13, in which said proximal and distal regions are of substantially the same radius about their respective centers.

15. An intubating laryngeal-mask airway device, comprising an airway tube having a fixed curve of substantially constant radius in a first geometric plane, the fixed curve is configured to conform to an anatomical curve in a patient between a proximal end at approximately the location of a hard palate and a distal end at approximately a laryngeal inlet, said fixed curve having an arc of an angular extent between 100° and 145°, and mask structure of yieldable material at said distal limit, said rigid tube including a proximal end portion integrally formed with and tangentially related to the proximal limit of said fixed curve;
   said mask structure comprising a backing plate having a generally elliptical periphery in essentially a second geometric plane which is perpendicular to said first geometric plane, said periphery being adapted for sealing conformance to the laryngeal inlet, said mask structure having an airway passage through said backing plate (i) in said first geometric plane and (ii) at a first acute angle so said second geometric plane and (iii) connected to the distal limit of said tube, said mask structure including a ramp in the path of advancing intubation beyond the distal limit of said tube, said ramp being adapted to centrally stabilize intubation upon exit from the distal end of the curved portion of said rigid airway tube and in a direction toward the glottic opening, the included angle of incubation direction, upon exit from said ramp, being in the range of 130°±5° with respect to the orientation of said tangentially related proximal end portion.

16. The device of claim 15, in which said mask includes a compliantly hinged tongue that is normally disposed diametrically across the distal end of said path and is adapted to deflect the epiglottis upon advance of intubation beyond said distal end.

17. The device of claim 15, in which the distal end of said tube has a telescoping fit to the airway passage of said backing plate, and in which said distal end is truncated at a second acute angle to said second geometric plane, the direction of said second acute angle with respect to said second geometric plane being opposite to the direction of said first acute angle with respect to said second geometric plane.

18. The device of claim 15, in which the tangentially related proximal-end portion of said tube is straight.

19. The device of claim 15, in which said tube has an outer-surface cladding of yieldable elastomeric material.

20. The device of claim 15, in which an inflatable ring continuously surrounding and connected to the periphery of said backing plate is adapted for sealing conformance of said mask structure to the laryngeal inlet.

21. An intubating laryngeal mask airway device including a continuous lumen for ventilating service to a patient's laryngeal inlet, extending from a proximal end to a distal end, the device including a proximal end portion extending from the proximal end of the device to a first location, the first location being closer to the proximal end of the device than to the distal end, a rigid airway tube extending from the first location to a second location, the second location being located between the first location and the distal end of the device and being closer to the distal end of the device than to the proximal end, the airway tube having a fixed curve of substantially constant radius between said first location and said second location, said fixed curve having an arc of an angular extent between 100° and 145°, and a laryngeal mask extending from the second location to the distal end of the device, said laryngeal mask having a generally elliptical periphery adapted for sealed engagement to the patient's laryngeal inlet, the periphery in a plane perpendicular to the fixed curve of the airway tube.

22. The device of claim 21, wherein the angular extent between the first location and the second location is in the range of 130°±5°.

23. The device of claim 21, wherein the first location is adjacent the longitudinal center of the patient's hard palate.

24. The device of claim 21, wherein the second location is adjacent the patient's glottic aperture.

25. The device of claim 21, wherein the laryngeal mask is of yieldable material.

26. The device of claim 21, wherein the device is adapted to telescopically receive an endotracheal tube.

27. The device of claim 21, wherein the laryngeal mask further includes a ramp in the lumen adapted to facilitate entrance of an endotracheal tube advancing through the opening of the lumen of the device into the patient's glottic aperture.

28. The device of claim 27, wherein the ramp includes a groove adapted to guide and support the endotracheal tube.

29. An intubating laryngeal mask airway device including a continuous lumen for ventilating service to a patient's laryngeal inlet, extending from a proximal end to a distal end, the device including a proximal end portion extending from the proximal end of the device to a first location, the first location being closer to the proximal end of the device than to the distal end, a rigid airway tube extending from the first location to a second location, the second location being located between the first location and the distal end of the device and being closer to the distal end of the device than to the proximal end, the airway tube being curved along a fixed curve between said first location and said second location, said fixed curve having an arc of an angular extent between 100° and 145°, and a laryngeal mask extending from the second location to the distal end of the device, said laryngeal mask having a generally elliptical periphery adapted for sealed engagement to the patient's laryngeal inlet, the periphery in a plane perpendicular to the fixed curve of the airway tube,
wherein the laryngeal mask further includes a ramp in the lumen adapted to facilitate entrance of an endotracheal tube advancing through the opening of the lumen of the device into the patient's glottic aperture, the ramp further including a groove adapted to guide and support the endotracheal tube,
wherein the laryngeal mask further includes a compliantly hinged tongue formation having a diameter that is smaller than the diameter of the lumen.

30. The device of claim 29, wherein the advancement of the endotracheal tube deflects the tongue formation.

31. The device of claim 29, wherein the airway tube is constructed of stainless steel.

32. The device of claim 29, wherein the airway cube is coated with an elastomeric material.

33. The device of claim 29, wherein the fixed curve is circular with a substantially constant radius.

34. The device of claim 29, wherein the fixed curve is elliptical with two radii, a line connecting the centers of the two radii being essentially parallel to the alignment of the patient's vertebrae.

35. The device of claim 29, wherein the lumen has 13 mm minimum diameter.

36. An intubating laryngeal mask airway device comprising:
an airway tube having a fixed curve of substantially constant radius, said fixed curve configured to conform to an anatomical curve in a patient between a proximal end at approximately the location of a hard palate and a distal end at approximately a laryngeal inlet, said fixed curve having an arc of an angular extent between 100° and 145°, said airway tube adapted to be attached to a gas source outside the patient; and
an inflatable mask structure attached to the distal end of the airway tube, said mask structure providing an air tight seal around the laryngeal inlet when inflated, the airway tube defining a lumen adapted to provide gas from the gas source to the laryngeal inlet.

37. The intubating laryngeal mask airway device of claim 36, which the proximal-end portion of said tube has at least a portion that is straight.

38. The intubating laryngeal mask airway device of claim 36, in which said tube has an outer-surface cladding of yieldable elastomeric material.

39. The intubating laryngeal mask airway device of claim 36, in which said fixed curve includes an intermediate locale for which a geometric tangent to said fixed curve is substantially parallel to adjacent patient backbone alignment, and in which an otherwise continuous arcuate development of said fixed curve is divided into proximal and distal regions which are integrally and tangentially formed with a substantially straight intermediate region of predetermined extent that is substantially parallel to said adjacent patient backbone alignment.

40. The intubating laryngeal mask airway device of claim 39, in which said proximal region is arcuate about a first center in said first geometric plane and said distal region is arcuate about a second center in said first geometric plane, said centers being spaced from each other on a geometric alignment which is substantially parallel to said substantially straight intermediate region.

41. The intubating laryngeal mask airway device of claim 40, in which said proximal and distal regions are of substantially the same radius about their respective centers.

42. The intubating laryngeal mask airway device of claim 36, wherein the fixed curve is circular with substantially constant radius.

43. The intubating laryngeal mask airway device of claim 36, wherein the fixed curve is elliptical with two radii, a line connecting the centers of the two radii being essentially parallel to the alignment of the patient's vertebrae.

44. The intubating laryngeal mask airway device of claim 36, wherein the lumen has a 13 mm minimum diameter.

45. An intubating laryngeal mask airway device comprising:

an airway tube having a fixed curve, the fixed curve is configured to conform to an anatomical curve in a patient between a proximal end at approximately the location of a hard palate and a distal end at approximately a laryngeal inlet, said airway tube adapted to be attached to a gas source outside the patient;

said fixed curve including an intermediate locale for which a geometric tangent to said fixed curve is substantially parallel to adjacent patient backbone alignment, and in which an otherwise continuous arcuate development of said fixed curve is divided into proximal and distal regions which are integrally and tangentially formed with a substantially straight intermediate region of predetermined extent that is substantially parallel to said adjacent patient backbone alignment, said proximal region having a first arc of a first angular extent and said distal region having a second arc of a second angular extent, the sum of said first angular extent and said second angular extent being between 100° and 145°; and an inflatable mask structure attached to the distal end of the airway tube, said mask structure providing an air tight seal around the laryngeal inlet when inflated, the airway tube defining a lumen adapted to provide gas from the gas source to the laryngeal inlet.

46. The device of claim 45, in which said proximal region is arcuate about a first center and said distal region is arcuate about a second center, said centers being spaced from each other on a geometric alignment which is substantially parallel to said substantially straight intermediate region.

47. The device of claim 46, in which said proximal and distal regions are of substantially the same radius about their respective centers.

* * * * *